Figure 1:
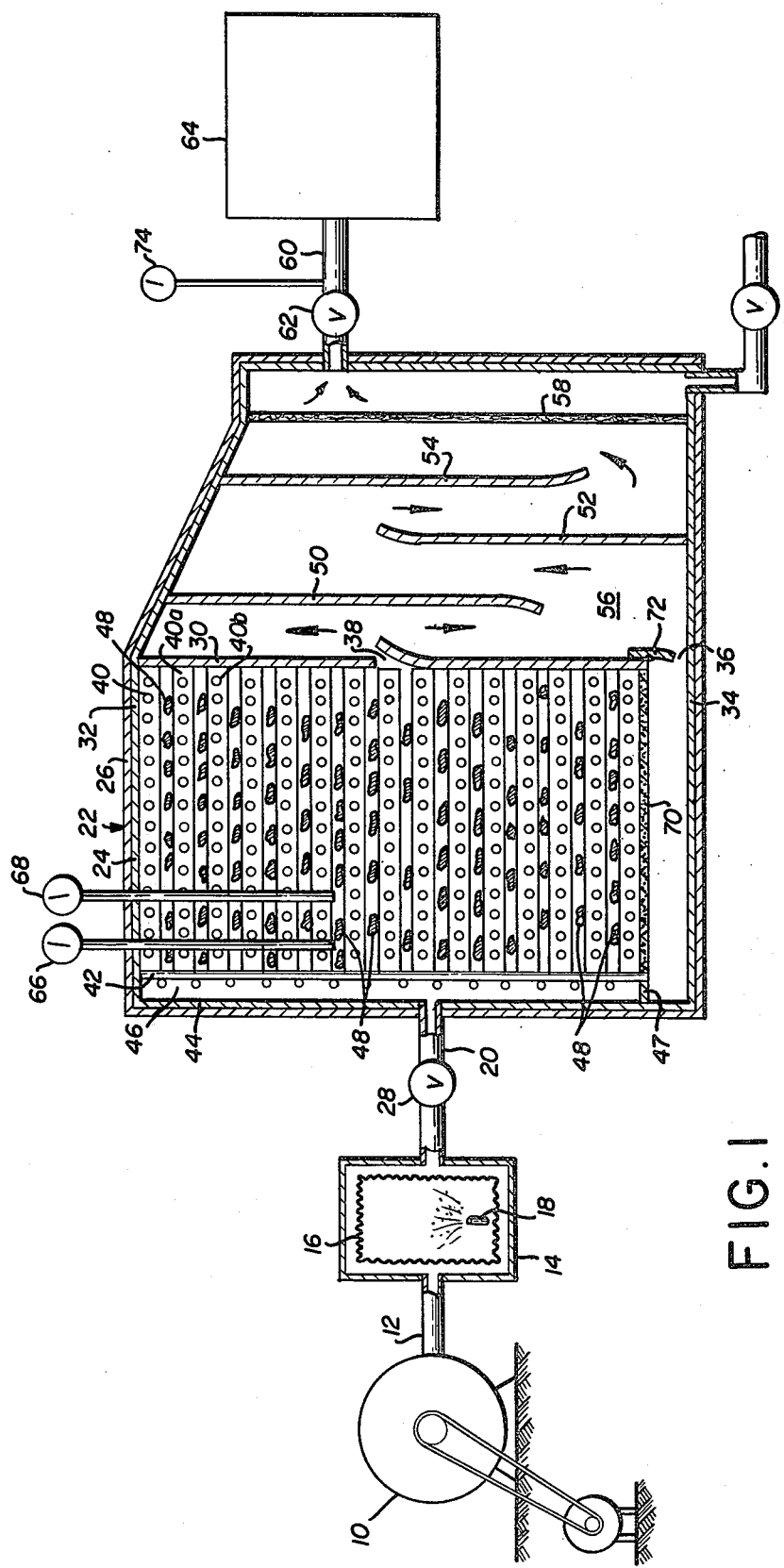

United States Patent [19]

Tateno

[11] 4,386,276
[45] May 31, 1983

[54] METHOD AND APPARATUS FOR PRODUCING AN IONIZED GAS BY RADIATION

[76] Inventor: Sinjitsu Tateno, 3-8 Nagara-sakurai-cho, Gifu City, Japan

[21] Appl. No.: 318,035

[22] Filed: Nov. 4, 1981

Related U.S. Application Data

[63] Continuation-in-part of Ser. No. 63,207, Aug. 3, 1979, abandoned, which is a continuation-in-part of Ser. No. 806,912, Jun. 15, 1977, abandoned.

[51] Int. Cl.³ .............................................. G01N 23/00
[52] U.S. Cl. ................................. 250/436; 250/432 R
[58] Field of Search ............... 250/432, 436, 437, 427, 250/429, 492 R

[56] References Cited

U.S. PATENT DOCUMENTS

| | | | |
|---|---|---|---|
| 2,003,898 | 6/1935 | Mitscherling | 250/436 |
| 2,945,951 | 7/1960 | Bright | 250/427 |
| 3,655,982 | 4/1972 | Gelezumas | 250/432 R |

Primary Examiner—Bruce C. Anderson
Attorney, Agent, or Firm—Bernard Olcott

[57] ABSTRACT

A method and apparatus for producing an ionized gas by exposure to a source of alpha radiation. Propelled gas from a blower is selectively subjected to controlled humidity and temperature. The gas is then passed over a source of alpha radiation. Thereafter the radioactivity of the gas is removed by suitable shielding. The resulting ionized gas is useful for restoring or improving the edibility and taste of liquid and solid food products.

8 Claims, 2 Drawing Figures

METHOD AND APPARATUS FOR PRODUCING AN IONIZED GAS BY RADIATION

This application is a continuation-in-part application of Ser. No. 63,207, filed Aug. 3, 1979, now abandoned, which is a continuation-in-part of Ser. No. 806,912, filed June 15, 1977, now abandoned.

This invention is directed to improved methods and apparatus using radioactive ores for the production of an ionized gas with substantially no radioactive contamination.

A principal object of the invention is to improve the production of an ionized gas by exposing a gaseous source to radioactive ores and to remove from the exposed gas undesirable radioactivity.

Another object of this invention is to improve the edibility of foods which have become spoiled, or partially spoiled, by passing of time.

Another object of this invention is to provide an improved method and apparatus for improving the color and taste of beef and tuna fish which has been contaminated by bacteria by normal aging phenomena.

Another object of this invention is to provide an improved method and apparatus for improving the taste, color and fragrance of spirits such as whiskey, wine and beer.

In accordance with the invention disclosed herein is an apparatus for the production of an ionized gas comprising a gas propelling device, container means coupled to the outlet side of the device for selectively controlling humidity and temperature of the gas passing therethrough, a reaction chamber coupled at its inlet side to the outlet side of the container means, supporting means within the reaction chamber for a radioactive substance therein capable of generating alpha radiation, and means coupled to the outlet side of the reaction chamber for substantially removing the radioactivity from the resulting humidity and temperature controlled gas which has been subject to alpha radiation. In accordance with the invention disclosed herein is a method for the production of an ionized gas comprising the steps of passing a gas having selected temperature and selected humidity over a radioactive substance which generates alpha radiation and substantially removing the radioactivity from the gas which has been subject to alpha radiation.

Figure 2:
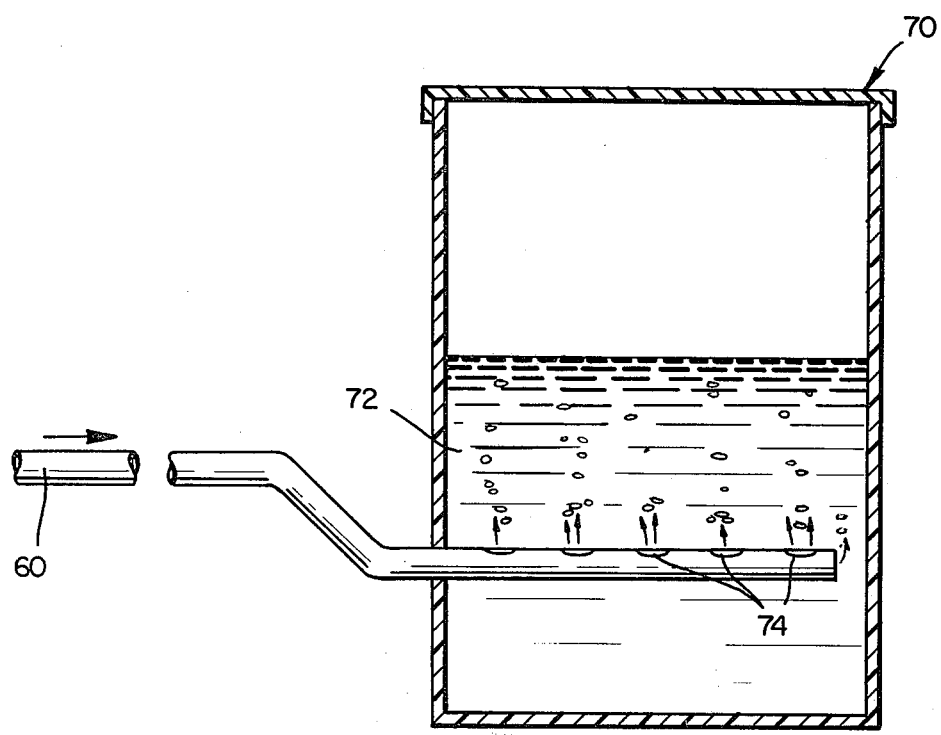

The invention will be more fully understood by reference to the following detailed description which is accompanied by drawings in which:

FIG. 1 illustrates one embodiment of the invention to produce an ionized gas with substantially no radioactive contamination; and FIG. 2 shows a modification of FIG. 1 to provide an ionized water solution without radio activity contamination.

In FIG. 1, a motor driven air compressor 10 is connected at its output end by a pipe 12 to a humidifying and heating chamber 14 having a heater element 16 and a water injector 18. At the outlet end of 14 is a pipe 20 which connects to a radioactive ore chamber 22 having lead walls 24 surrounded by a stainless steel jacket 26. A valve 28 in pipe 20 controls the air flow from the compressor 10 through the heating and humidifying chamber 14 and into the radioactive ore chamber 22. Heater 16 and water injector 18 are actuated and controlled in the known matter by apparatus not shown.

In the interior region of 22 is a lead wall 30 extending from a top wall 32 of 22 downwardly towards but not reaching a bottom wall 34 of 22. The transverse width of wall 30 extends from side wall to side wall (not shown) of 22 so as to form a recirculating passageway 36 between the regions to the left and right of wall 30. Wall 30 has an orifice 38. Wall 30 supports one end of a plurality of spaced wire mesh screens or shelves 40, 40a, 40b, etc. The other ends of spaced screens 40, 40a, 40b, etc. are supported by a plurality of spaced struts 42 to permit the compressed air in pipe 20 to flow out orifice 38 in lead wall 30. The struts 42 and the adjacent ends of screens 40, 40a, 40b, etc. are spaced from an end wall 44 of 22 so as to form a compressed inlet air distribution passageway 46 which is sealed off by a plate 47 from the recirculating passage 36 at the bottom region of 22.

Relatively weak, low grade, radioactive ore 48 which emits alpha ions is placed on the screen 40, 40a, 40b, etc. through openings, not shown for simplicity sake, in chamber 22.

The humidified and heated air after flowing over the low grade radioactive ore 48 exits through orifice 38 and is confined by lead baffles 50, 52 and 54 in a multi turn circuitous passage 56 and through a filter 58 to reach an exit pipe 60 having a valve 62. Such lead baffles attenuate and finally remove substantially all of the radioactivity. Pipe 60 empties into an ionized air collecting chamber 64. The recirculating passage 36 opens to the exit passage 56 and a portion of the air leaving the orifice 38 is returned again to pass over the ore 48 through a bed of sand 70. The quantity of the recirculated stream is controlled by an adjustable vane 72. A thermostat 66, humidistat 68 in chamber 22 and a flow meter 74, together with the valve 28 and 62 and vane 72 permit the operator to control the temperature and humidity of the air passing over the ore 48 and the strength of ions in chamber 64.

Tests have shown that the method and apparatus of the present invention can produce four to five times the quantity per unit volume of ionized gas as is normally available from weak low grade ores and without radioactivity contamination.

EXPERIMENT NO. 1

For five samples 1, 2, 3, 4 and 5 of Monazite ore, $ThO_2$ 2.5%, having thorium radioactivity of $0.002\mu$ c/g, the quantity of ions per unit volume in chamber 64 were measured as follows:

| Sample No. | Humidity | Temperature (°C.) | Ions Measured (Cpm) |
|---|---|---|---|
| 1 | 65 | 20 | 125 |
| 2 | 84 | 20 | 245 |
| 3 | 100 | 50 | 400 |
| 4 | 100 | 60 | 500 |
| 5 | 100 | 70 | 700 |

A laboratory measurement and analysis of the ionized gas in chamber 64 revealed no radioactivity.

Other tests were made under the following conditions:

Air movement by blower 10: 15 liters/min

Ore 48: Thorium compound ($ThO_2$ 20%), 5 g, 800 CPM

EXPERIMENT NO. 2

Relation between the change in temperature and the quantity of ions.

| No. | Temp. (°C.) | Pressure (kg/cm$^2$) | Air Amount (l/min.) | Measured value of ion (cpm) |
|---|---|---|---|---|
| 1 | 40 | 1.1 | 10 | 240 |
| 2 | 45 | 1.1 | 10 | 300 |
| 3 | 50 | 1.1 | 10 | 400 |
| 4 | 52 | 1.1 | 10 | 450 |
| 5 | 60 | 1.1 | 10 | 500 |
| 6 | 65 | 1.1 | 10 | 600 |
| 7 | 70 | 1.1 | 10 | 700 |

EXPERIMENT NO. 3

Relation between the change in humidity and temperature and the quantity of ions.

| No. | Humidity (%) | Temp. (°C.) | Air Amount (l/min.) | Measure value of ion (cpm) |
|---|---|---|---|---|
| 1 | 60 | 20 | 10 | 120 |
| 2 | 85 | 20 | 10 | 240 |
| 3 | 95 | 20 | 10 | 260 |
| 4 | 100 | 40 | 10 | 320 |
| 5 | 100 | 50 | 10 | 380 |

One application of the apparatus disclosed in FIG. 1 is to place beef, tuna and similar foods which have been discolored, or spoiled, or semi spoiled, by the passing of time and/or by insufficient refrigeration into the collecting chamber 64. Such contaminated foods improved in color, appearance, taste and smell.

As shown in FIG. 2, the exit pipe 60 of FIG. 1, which can be a plastic tube, is optionally connected to a closed tank 70 containing water 72. The pipe 60 is connected to bubble the moving gas containing the ionized gas from reaction chamber 22 under the surface of water 72 by way of orifices 74 in pipe 60. The tank 70 is preferably black or opaque to promote the preservation of the ionized water which is preferably stored at a low temperature. The tank 70 is preferably covered so that the relative humidity therein may rise up to 95% to 99%. It is believed that the vapor particles therein collide with the ions issuing from orifices 74 in pipe 60 and that the quantity of ionized water is increased by repeated collisions.

The quality of the ionized water can be improved after storage by exposure to ultra violet rays or the light of a fluorescent lamp.

The manufactured ionized water of FIG. 2 without contamination has many uses by industry, laboratory technicians and the medical profession. Also, the bubbling of the ionized gas from orifices 74, through beer and whiskey has been found to improve its fragrance, color and taste.

EXPERIMENT NO. 4

Using the apparatus of FIG. 2, ionized water was generated in a black opague tank 70 by bubbling ionized gas from FIG. 1 through water for 20 minutes. The water was transferred to a transparent beaker after forty eight hours. The change in pH was measured by a pH meter under 400 candles of florescent light (indoor illumination) as follows:

| (Min.) | (pH) | (Min.) | (pH) | (Min.) | (pH) |
|---|---|---|---|---|---|
| 1 | 7.10 | 11 | 7.59 | 21 | 7.66 |
| 2 | 7.20 | 12 | 7.60 | 22 | 7.66 |
| 3 | 7.27 | 13 | 7.61 | 23 | 7.66 |
| 4 | 7.32 | 14 | 7.61 | 24 | 7.66 |
| 5 | 7.39 | 15 | 7.62 | 25 | 7.67 |
| 6 | 7.44 | 16 | 7.63 | 26 | 7.67 |
| 7 | 7.48 | 17 | 7.64 | 27 | 7.67 |
| 8 | 7.51 | 18 | 7.64 | 28 | 7.67 |
| 9 | 7.52 | 19 | 7.65 | 29 | 7.67 |
| 10 | 7.56 | 20 | 7.66 | 30 | 7.67 |

While there has been described and pointed out the fundamental novel features of the invention as applied to a limited number of embodiments, it will be understood that various omissions and substitutes and changes in the form and details of the device illustrated and its operation may be made by those skilled in the art, without departing from the spirit of the invention. It is the intention, therefore, to be limited only as indicated by the scope of the following claims.

What I claim is:

1. Apparatus for producing an ionized gas which comprises a gas propelling device, container means coupled to the outlet side of said device for selectively controlling humidity and temperature of the gas passing therethrough, a reaction chamber coupled at its inlet side to the outlet side of said container means, supporting means within said reaction chamber for a radioactive substance therein capable of generating alpha radiation, and means coupled to the outlet side of said reaction chamber for substantially removing the radioactivity from the resulting humidity and temperature controlled gas subjected to alpha radiation passing therethrough.

2. Apparatus according to claim 1 wherein said reaction chamber includes a passage for recirculating at least a portion of the gas which exits from said reaction chamber and returning the recirculated gas again to pass through the reaction chamber.

3. Apparatus according to claim 2 including a first valve means between said container means and said reaction chamber and a second valve means at the outlet of said reaction chamber whereby the quantity and flow rate of gas subject to alpha radiation is selectively controlled.

4. Apparatus according to claim 1 including means coupled to said radioactivity removing means for collecting the gas exiting therefrom and adapted to receive contaminated food for exposure to said ionized gas.

5. Apparatus according to claim 1 including a conduit having one end coupled to said radioactivity removing means and a container adapted to hold liquid, the other end of said conduit being positioned near the bottom of said container to bubble said ionized gas through liquid in said container.

6. A method for producing an ionized gas which comprises the steps of: passing a gas having selected temperature and selected humidity over a radioactive substance which generates alpha radiation, and substantially removing the radioactivity from the gas subjected to alpha radiation.

7. Method according to claim 6 including the step of recirculating a portion of the gas back over said radioactive substance before the step of removing the radioactivity in the gas.

8. Method according to the claim 6 including the step of exposing the resulting non-radioactive gas stream to contaminated foods selected from a group consisting of tuna, beef, beer, wine, whiskey and water.

* * * * *